United States Patent [19]
Wroblewski et al.

[11] Patent Number: 4,783,192
[45] Date of Patent: Nov. 8, 1988

[54] JOINT PROSTHESIS

[76] Inventors: Boguslaw M. Wroblewski, The Coach House, Tanhouse Close, Parbold, Lancs, England, WN8 7HG; Philip Shelley, 35 Runshaw Avenue, Appleybridge, Wigan, England, WN6 9JP

[21] Appl. No.: 896,113

[22] Filed: Aug. 13, 1986

[30] Foreign Application Priority Data

Aug. 14, 1985 [GB] United Kingdom ............... 8520360

[51] Int. Cl.$^4$ .......................... A61F 2/28; A61F 2/30
[52] U.S. Cl. ...................................... 623/16; 623/18; 623/23
[58] Field of Search ............................... 623/16–23

[56] References Cited

U.S. PATENT DOCUMENTS

| | | | |
|---|---|---|---|
| 4,012,796 | 3/1977 | Weisman et al. | 623/18 |
| 4,578,081 | 3/1986 | Harder et al. | 623/18 |
| 4,619,659 | 10/1986 | Witzel | 623/18 |

FOREIGN PATENT DOCUMENTS

| | | | |
|---|---|---|---|
| 2153233 | 7/1985 | European Pat. Off. | 623/16 |
| 0158014 | 10/1985 | European Pat. Off. | 623/22 |
| 2724234 | 12/1977 | Fed. Rep. of Germany | 623/23 |
| 8302555 | 8/1983 | PCT Int'l Appl. | 623/22 |
| 0492277 | 11/1975 | U.S.S.R. | 623/23 |

Primary Examiner—Richard J. Apley
Assistant Examiner—David Isabella
Attorney, Agent, or Firm—Henry Sternberg; Bert J. Lewen

[57] ABSTRACT

A joint prosthesis for use in long bone joint replacement comprises a tapering stem 4 upon which is located a collar 10 chosen from a range of similar collars having different internal diameters. The collar chosen locates with the stem at a particular height, depending on the internal diameter of the collar and the tapering of the stem.

12 Claims, 4 Drawing Sheets

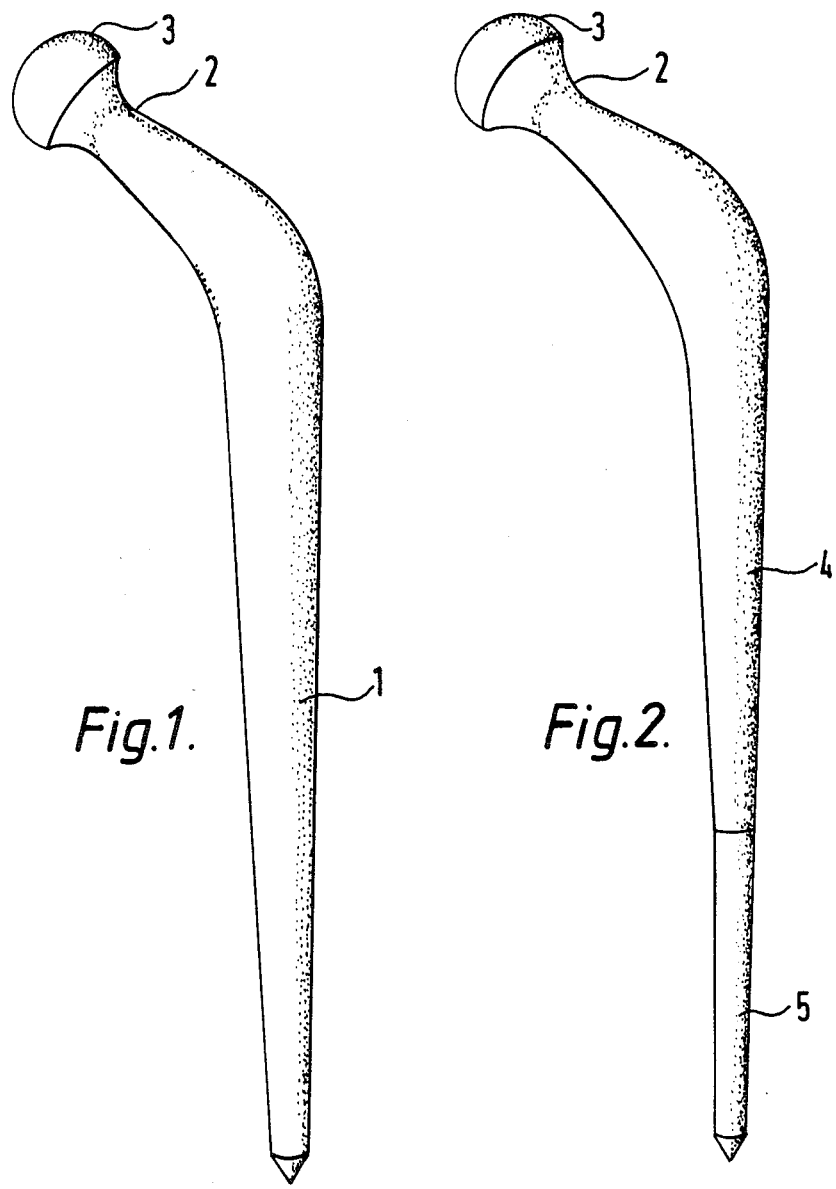

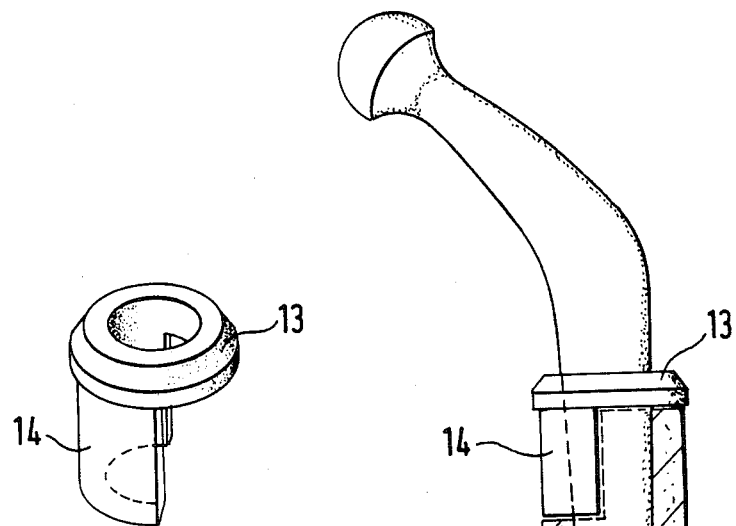
Fig.5.
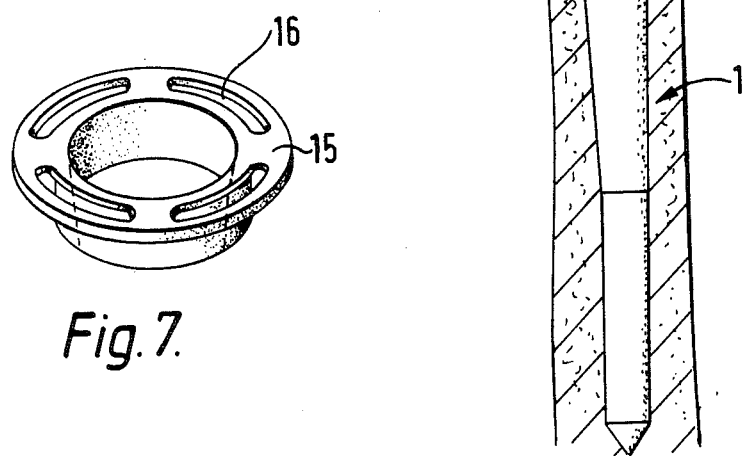
Fig.7.
Fig.6.

JOINT PROSTHESIS

The present invention relates to prostheses, particularly to prostheses used in joint replacement surgery, and more particularly to joint replacement prostheses for use in situations where there has been loss of bone at or around the joint to be replaced.

In situations where there has been loss of bone for any reason, there is a need to replace this loss with a suitably shaped and structured prosthesis. This may also be necessary in cases of tumours, infective destruction of tissue, or adverse tissue reaction to implants or debris. Such cases, in which a special "custom made" prosthesis is required, are now becoming more common due to the growth in operative intervention in the joint replacement field.

At present, this need is met by the manufacture of custom made prostheses which accommodate a fixed level of bone resection as determined from radiographs taken prior to surgery. At the time of surgery, the bone must then be resected accurately in order to fit the prosthesis, leaving very limited room for error and no facility to adjust limb length or joint stability during the surgery. This method suffers for the disadvantage that the degree of resection or bone to be erected needs to be decided prior to surgery, merely from analysis of the radiographs, without any knowledge of bone quality or vitality.

According to the present invention there is provided a prosthesis for use in long bone joint replacement, the prosthesis including a stem for inserting within a bone adjacent a joint to be replaced, the stem being tapered over at least a part of its length, and at least one collar for fitting around the stem, the or each collar having an inner stem-engaging surface and an outer bone-engaging surface and locating with the stem at a height determined by the internal diameter of the collar and the tapering of the stem.

Preferably the or each collar forms part of a range of collars having different internal diameters to suit the requirements of individual patients.

Thus the prosthesis of the present invention, by offering a choice of different collars, each locating at a different pre-set height on the stem, gives the surgeon control of the limb length, joint stability and degree of resection. The prosthesis of the present invention may be applied to any long bone joint replacment, for example, the shoulder, finger, elbow or hip joints. Once in position within the bone, the collar fitted on the stem prevents axial subsidence of the stem by providing means of load transfer to the bone.

The stem may comprise a single portion which tapers along the whole of its length, or alternatively it may comprise a first tapering portion which blends into a second portion of constant dimensions. In the case of a joint replacement prosthesis, the stem would normally include means carrying a bearing surface, such as that of a femoral head in the case of a hip joint prosthesis, for articulating with a corresponding surface of an acetabular component of the prostheses.

Preferably the stem is provided with flat sides or grooves to prevent rotation of the stem within the bone.

The flat sides or grooves may in themselves be tapered.

Each collar of the range may be circular, or alternatively it may be shaped to accomodate the variations of bone anatomy along its length.

Each collar of the range may be lined on either or both of its stem-engaging and bone-engaging surfaces with a shock absorbing material such as plastics material to reduce stress concentrations in the stem and/or bone to collar interface.

The collars may be locking or non-locking. The locking collars are lockable into position at a pre-set height on the stem, and the non-locking collars are free to rotate and/or slide axially with respect to the stem. The locking collars are rotatable with respect to the stem prior to locking into position on the stem.

Most muscle attachments can be found near to the ends of long bones. In cases where bone resection has been carried out, it is often found that important muscle groups are devoid of an attachment to the bone.

Each collar of the range may include a means for attaching muscle groups thereto, or alternatively an extra and separate collar may be added with a muscle attachment capability.

Preferably the type of muscle attachment may be varied according to the individual requirements of the patient by selection of an appropriate collar having msucle attachment means.

A common problem occurs when there is only partial resection of the bone, for example where there is bone loss only on one side of the bone.

According to the present invention there is furtehr provided a prosthesis adapted for use in cases where there has been partial resection of the bone, in which the or each collar is provided with a downwardly depending bone load bearing portion extending some distance along the stem.

Thus, since the collars may be rotated with respect to the stem before they are locked in position, the radial position of bone loss ceases to be an important factor.

Embodiments of the present invention will now be described by way of example only with reference to the accompanying drawings in which:

FIG. 1 is a side view of a stem of a prosthesis in accordance with the present invention, the stem being tapered along all of its length;

FIG. 2 is a side view of an alternative stem of a prosthesis in accordance with the present invention, the stem being tapered over only a part of its length;

FIG. 5 is a perspective view of a locking collar of a prosthesis in accordance with the present invention;

FIG. 6 is a side view of the collar shown in FIG. 5 fitted to the stem shown in FIG. 2; and, FIG. 7 is a perspective view of a collar of a prosthesis in accordance with the present invention, the collar including muscle attachment means.

Figure 2A:
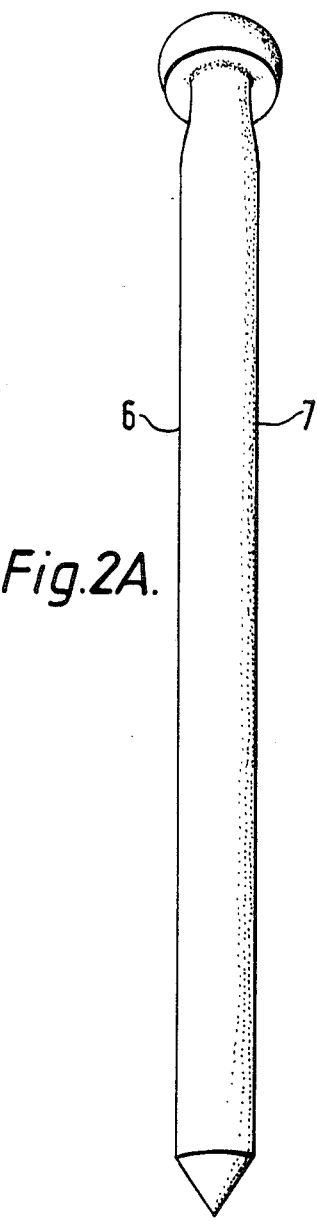
FIG. 2A is a back view of a stem of a prosthesis in accordance with the present invention, the stem having two parallel flat sides.

With reference to FIGS. 1 and 2 of the accompanying drawings, embodiments of the present invention will now be described using the example of a hip replacement prosthesis.

A femoral component of a hip replacement prosthesis comprises a stem 1, a neck 2 and a head 3. The stem 1 may be tapered along the whole of its length as shown in FIG. 1, or alternatively it may be tapered over a first proximal portion 4, blending into a distal portion 5 of constant width, as shown in FIG. 2.

Figure 2B:
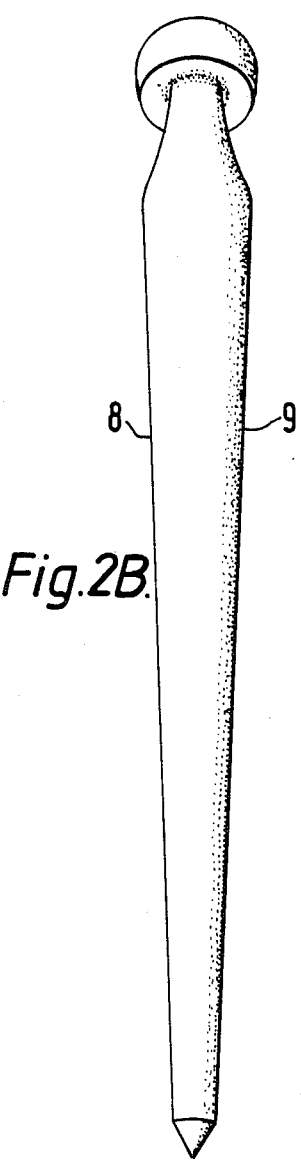
FIG. 2B is a back view of a stem of a prosthesis in accordance with the present invention, the stem having tapering flat sides.

Referring to FIGS. 2A and 2B, viewed from its other aspect, the stem may have parallel flat sides 6, 7, as shown in FIG. 2A, to prevent rotation of the stem within the cement or bone. The flat sides may themselves be tapered as indicated by sides 8, 9 of FIG. 2B. Alternatively, the stem may be provided with grooves (not shown) to prevent rotation of the stem within the cement or bone, the grooves themselves being either parallel or tapered.

Figure 3:
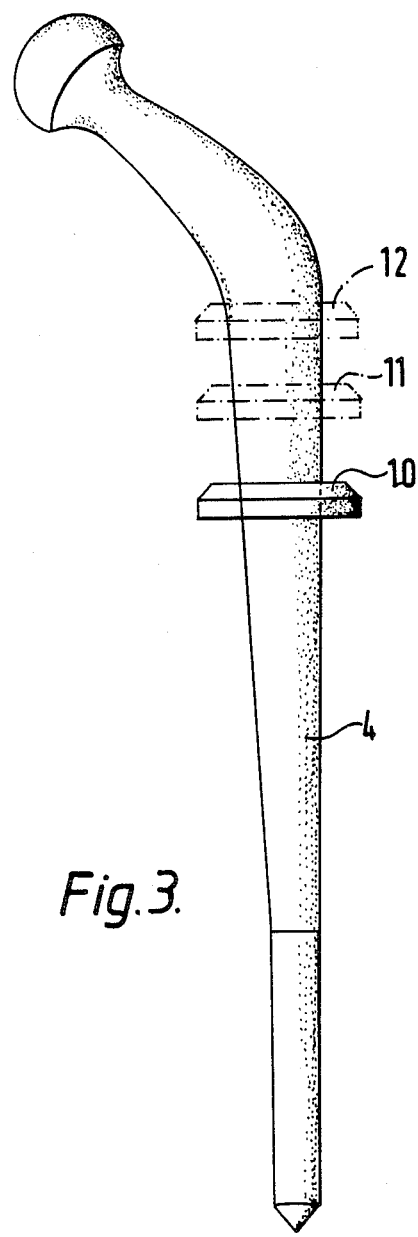
FIG. 3 is a side view of a collar of a prosthesis in accordance with the present invention, the collar being fitted to the stem shown in FIG. 2.
Figure 4:
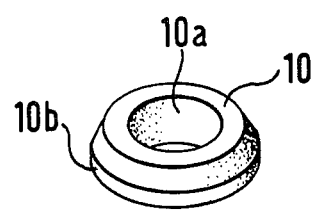
FIG. 4 is a perspective view of a collar of a prosthesis in accordance with the present invention.

With reference to FIGS. 3 and 4, a collar 10 in accordance with the present invention is annular with a stem-engaging surface 10a and a bone-engaging surface 10b. The collar 10 may be circular as shown in FIGS. 3 and 4, or alternatively it may be shaped to accommodate the variations of bone anatomy along its length (not shown).

The collars may be lined with a shock absorbing material such as plastics material on either or both of the surfaces 10a, 10b, thus reducing stress concentrations in the stem and/or bone to collar interface.

A variety of collars 10 having different diameters of the surface 10a allow each collar to be fitted around the stem to engage the stem at a different pre-set height, as indicated by positions 11, 12, i.e. each collar has a constant internal diameter which substantially exceeds the axial extent of the corresponding collar, such that inner stem-engaging surface 10a makes line contact with the tapering portion 4 of the stem 1 at an axial level of the stem at which the stem has the same diameter as that of the surface 10a (see FIG. 3). Thus the surgeon has control over limb length, joint stability and degree of resection by selection of an appropriate collar. The tapering portion 4 of the stem is machined accurately to permit a range of collars to be fitted to the stem.

The collar 10 may be of the non-locking or locking type. A locking collar may be locked into position at a pre-set height on the stem, whereas a non-locking collar is able to rotate and/or slide axially with respect to the stem 1. The locking collars are rotatable with respect to the stem prior to locking into position on the stem.

Another type of collar in accordance with the present invention is shown in FIGS. 5 and 6, this type of collar being suitable for cases in which there has been partial resection of the bone, for example when there is bone loss on only one side of the femur, perhaps due to damage resulting from a previous failed hip replacement. In this case, a locking collar 13 is located at or close to the top of the stem 1. The collar 13 includes a downwardly depending bone load bearing portion 14 which is some distance distal from the top of the stem 1. The collar may be rotated prior to locking into position, so that the radial position of the partial bone loss is not important.

A collar having a muscle attachment capability is shown in FIG. 7, and has a radially extending lip 15 with a number of slots 16 contained in the lip. These slots 16 provide muscle attachment points. This type of collar is useful in cases of bone resection where important muscle groups near the ends of long bones are devoid of attachment points to the bone. The apertures in the collar may be varied to suit the individual requirements of the patient.

We claim:
1. Prosthesis assembly for use in long bone joint replacement in a bone which has been resected or which has suffered bone loss in the region of the joint, comprising
   a joint component for replacing at least a part of the joint and having a stem for insertion within the bone, adjacent that part of the joint being replaced, to a selective height relative to the bone, which stem is tapered over at least a part of its length, and
   an associated series of disc-like annular collars correspondingly provided with respective internal circular collar openings in a range of different internal diameters, each collar having a constant internal diameter which substantially exceeds the axial extent of such collar, each collar opening forming an inner stem engaging surface, and each collar being further provided with a bottom outer bone engaging surface to lie on the resected or lost portion of the bone,
   such that each collar is locatable on the bone with its outer bone engaging surface abutting the resected or lost portion of the bone, and in turn is locatable on the stem at a collar height selectively determined by the constant internal diameter of the collar opening and the taper of the stem for correspondingly determining the selective height of the inserted stem relative to the bone, the inner stem engaging surface of the internal collar opening thereby making line contact with the stem at an axial level of the stem at which the stem has the same diameter as that of the internal collar opening.

2. Assembly of claim 1 wherein the stem is provided with an exterior formation to prevent rotation of the stem within the bone.

3. Assembly on claim 2 wherein the exterior formation includes flat sides on the stem.

4. Assembly of claim 2 wherein the exterior formation includes grooves on the stem.

5. Assembly of claim 1 wherein the stem is tapered along the whole of its length.

6. Assembly of claim 1 wherein the stem includes a first tapering position which blends into a second portion of constant dimension.

7. Assembly of claim 1 wherein each collar is lined on at least one of its stem engaging surface and bone engaging surface with shock absorbing material.

8. Assembly of claim 7 wherein the shock absorbing material is a plastic material.

9. Assembly of claim 1 wherein each collar is provided with means for locking the collar in position on the stem.

10. Assembly of claim 1 wherein at least one of the collars is provided with means for attaching muscle groups thereto.

11. Assembly of claim 1 wherein at least one of the collars is provided along a limited portion of its circumference with a downwardly depending bone load bearing side portion arranged for extending a selective distance along the stem, for use in cases where there has been only partial resection of bone.

12. Method of replacing at least part of a long bone joint, comprising
   selecting a joint component having a stem for insertion within the resected bone to a selective height relative to the bone, which stem is tapered over at least a part of its length,
   fitting onto the stem a collar selected from an associated series of disc-like annular collars correspondingly provided with respective internal circular collar-openings in the range of different internal diameters, each collar having a constant internal diameter which substantially exceeds the axial extent of such collar, each collar opening forming an inner stem engaging surface, and each collar being further provided with a bottom outer bone engaging surface to lie on the resected portion of the bone, such that each collar is locatable on the bone with its outer bone engaging surface abutting the resected portion of the bone, and in turn is locatable on the stem at a collar height selectively determined by the constant internal diameter of the collar opening and the taper of the stem for correspondingly determining the selective height of the inserted stem relative to the bone, the fitting being carried out whereby to locate the selected collar on the stem at a collar height for correspondingly locating the stem at the selective insertion height relative to the bone, the inner stem engaging surface of the internal collar opening thereby making line contact with the stem at an axial level of the stem at which the stem has the same diameter as that of the internal collar opening, and inserting the stem, bearing the selected collar at said collar height thereon, within the resected bone until the bone engaging surface of the collar engages the resected surface of the bone for correspondingly locating the stem at the selective insertion height relative to the bone.

* * * * *

UNITED STATES PATENT AND TRADEMARK OFFICE
CERTIFICATE OF CORRECTION

PATENT NO. : 4,783,192

DATED : November 8, 1988

INVENTOR(S) : Boguslaw M. Wroblewski et al.

It is certified that error appears in the above-identified patent and that said Letters Patent is hereby corrected as shown below:

Claim 3, line 34, delete "on" and substitute therefor --of--.

Claim 6, line 41, delete "position" and substitute therefor --portion--.

Signed and Sealed this

Seventh Day of March, 1989

Attest:

DONALD J. QUIGG

*Attesting Officer*     *Commissioner of Patents and Trademarks*